United States Patent [19]
Peppel et al.

[11] Patent Number: 5,945,607
[45] Date of Patent: Aug. 31, 1999

[54] TEST SPECIMEN HOLDER

[75] Inventors: Greg A. Peppel, Shakopee; Martin M. Gram, St. Louis Park; Vogel P. Grote, Jordan, all of Minn.; Kenneth L. Jerina, Clayton, Mo.

[73] Assignee: MTS Systems Corporation, Eden Prairie, Minn.

[21] Appl. No.: 08/873,640

[22] Filed: Jun. 12, 1997

[51] Int. Cl.[6] .................................................. G01N 3/08
[52] U.S. Cl. ................................ 73/856; 73/857; 73/831
[58] Field of Search .......................... 73/831, 833, 856, 73/857, 859, 860

[56] References Cited

U.S. PATENT DOCUMENTS

| 4,194,402 | 3/1980 | De Nicola | 73/859 |
|---|---|---|---|
| 4,721,000 | 1/1988 | Scanlon | 73/833 |
| 4,909,085 | 3/1990 | Hardy et al. | 73/833 |
| 5,054,324 | 10/1991 | Pohl | 73/859 |
| 5,095,757 | 3/1992 | Larsen et al. | 73/857 |
| 5,119,681 | 6/1992 | Miszczak | 73/831 |
| 5,237,876 | 8/1993 | Liu | 73/831 |
| 5,329,820 | 7/1994 | McMahon | 73/833 |
| 5,481,923 | 1/1996 | Ohmi et al. | 73/860 |
| 5,505,095 | 4/1996 | Raymon | 73/831 |
| 5,581,040 | 12/1996 | Lin | 73/833 |

FOREIGN PATENT DOCUMENTS

| 0 573 952 | 12/1993 | European Pat. Off. . |
|---|---|---|
| 2 378 273 | 8/1978 | France . |
| 19 20 767 | 11/1970 | Germany . |
| 1547552 | 1/1978 | United Kingdom . |

OTHER PUBLICATIONS

Catalog: "MTS Grips & Fixtures", MTS Systems Corporation, Eden Prairie, MN, 1995, pp. 1–44.

"Application Notes—New Grip Adapters for Low Cycle Fatigue Testing of Button–Head Specimens", MTS Systems Corporation, Eden Prairie, MN, 1991.

*Primary Examiner*—Max H. Noori
*Attorney, Agent, or Firm*—Westman, Champlin & Kelly, P.A.

[57] ABSTRACT

A test specimen holder for holding a test specimen in a material testing machine that applies force loads to the test specimen includes a base member having a first end coupleable to the material testing machine and a second end remote from the first end. A longitudinal axis extends from the first end to the second end. A body member extends from the second end to the first end and includes an aperture disposed on the longitudinal axis for receiving the test specimen. A displacement device displaces the body member relative to the base member substantially parallel to the longitudinal axis.

11 Claims, 12 Drawing Sheets

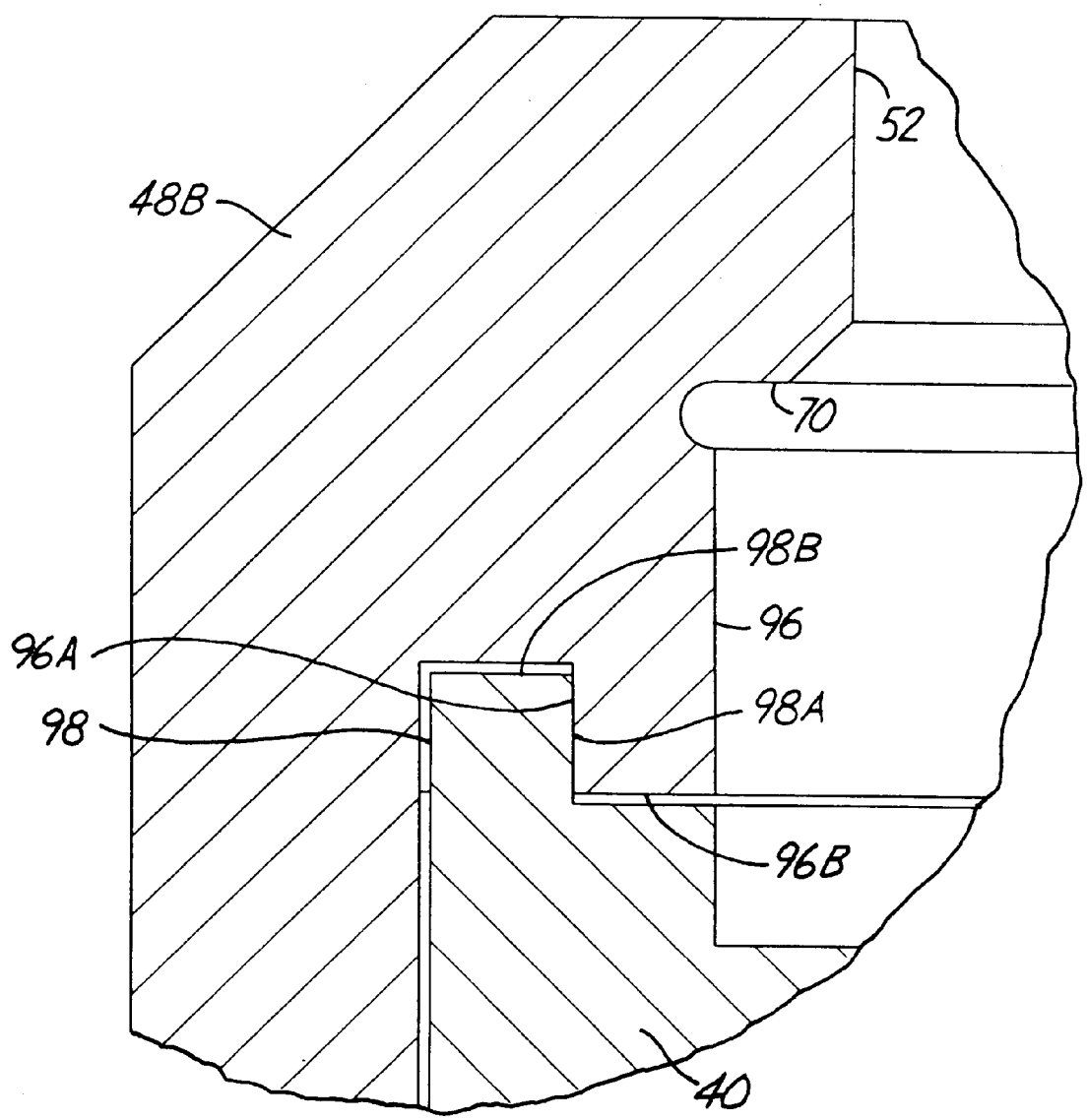

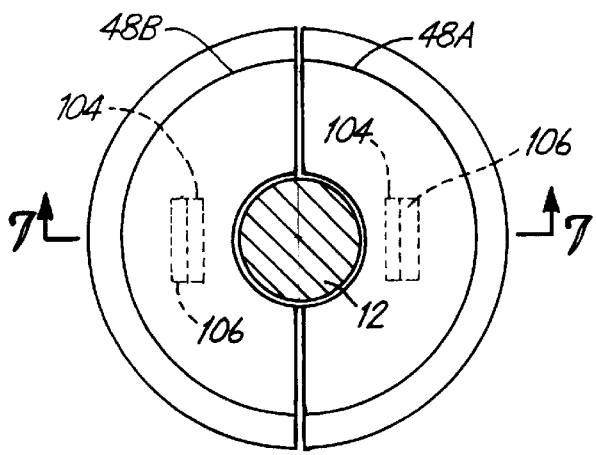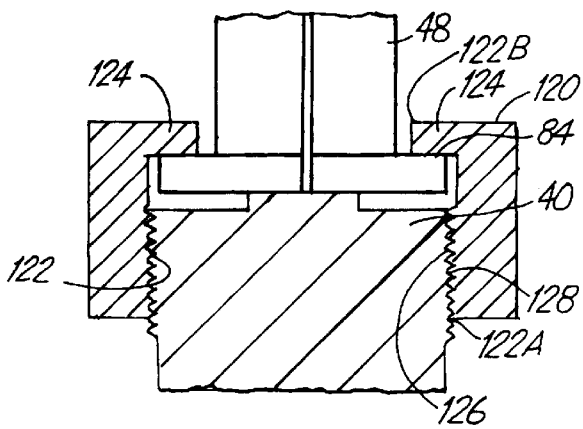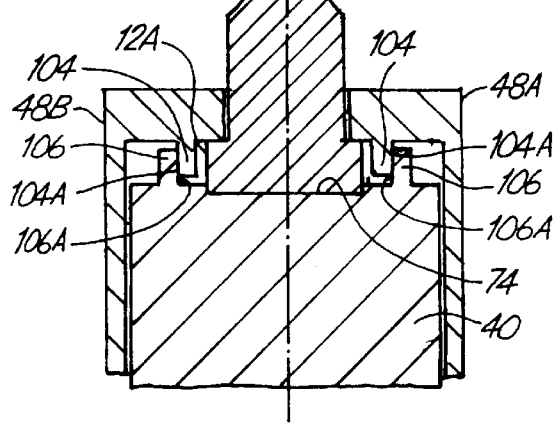

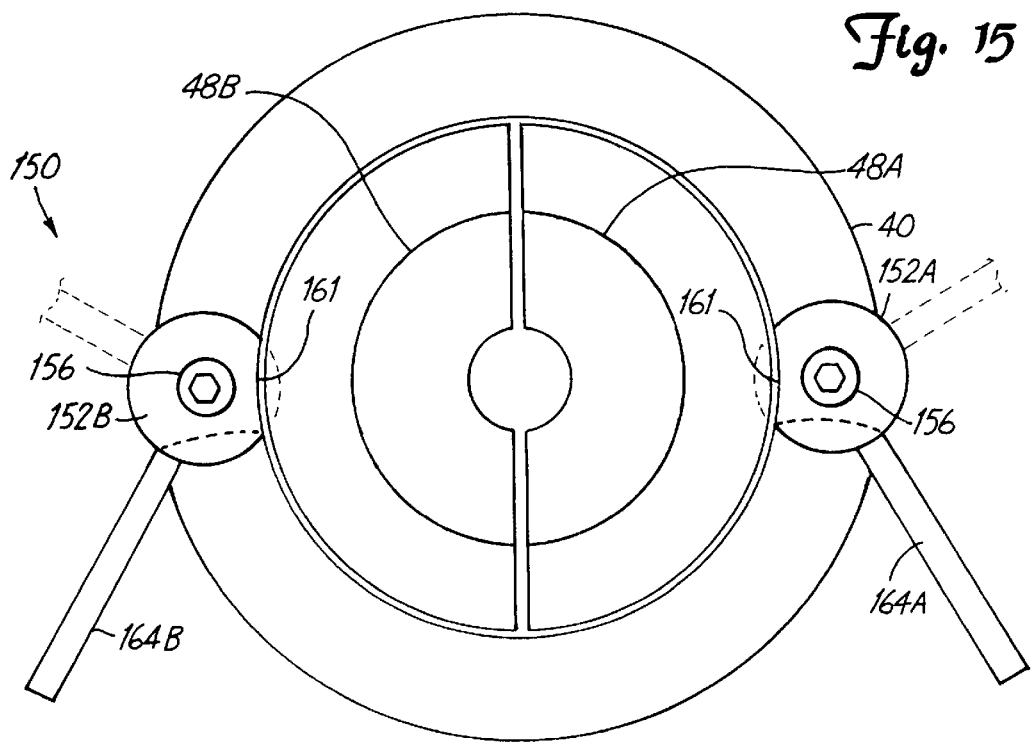
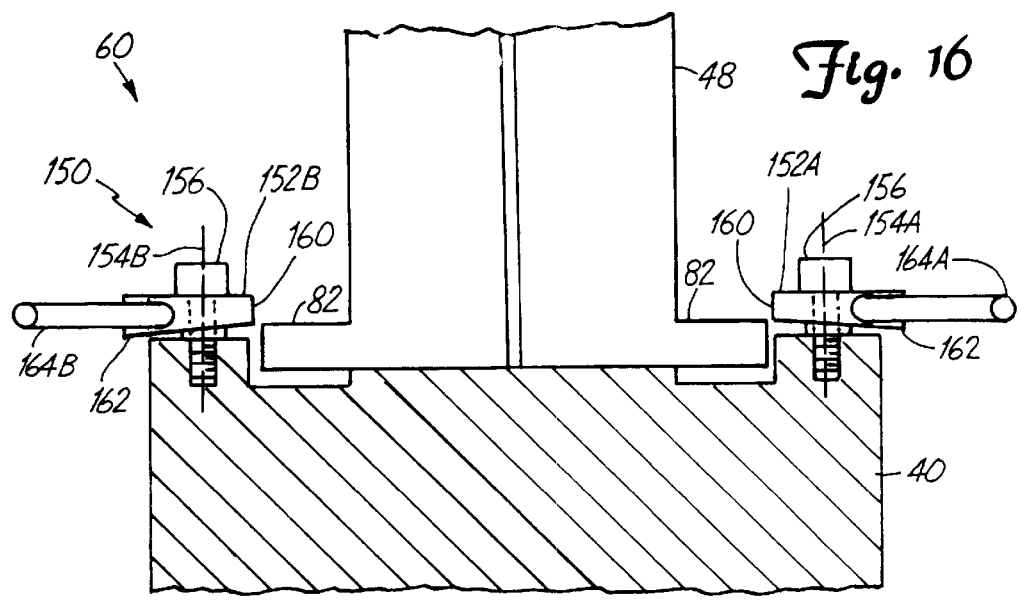

TEST SPECIMEN HOLDER

BACKGROUND OF THE INVENTION

The present invention relates to a material testing system that applies force loads to a test specimen. More particularly, the present invention relates to a test specimen holder that holds the test specimen in the material testing system.

Test specimen holders or grips are well known in the material testing art and are used frequently to hold a test specimen in a material testing system. One well known grip includes opposed jaws that grip the test specimen therebetween and slide upon converging surfaces of a support frame. These jaws grip the test specimen without altering the vertical position of the jaws on the test specimen, thereby making it possible to preselect the exact point at which the specimen will be held in order not to impart tension loads during placement of the test specimen and the material testing system. However, in order to hold the test specimen in place, substantial compressive forces must be applied to the test specimen from the jaws. When the test specimen is made from materials such as metals, compressive forces do not damage the test specimen. However, other test specimens are made from materials such as glass or ceramics which cannot accept substantial compressive holding forces. Thus, test specimen holders that incorporate jaws as described above cannot be used.

Commonly, test specimens made from brittle material such as glass or ceramics are elongated with enlarged ends. In the art, these specimens are known as "button-head specimens". Annular surfaces formed on the "buttons" are used to hold the test specimen and are used to apply test forces. One known assembly for holding a button-head test specimen in a material testing system includes mounting an adapter to a MTS 646 Hydraulic Collet Grip sold by MTS Systems Corporation of Eden Prairie, Minn. The adapter includes separable members that when joined together form a flange for engaging the annular surface of the button-head and an aperture through which the elongated portion of the test specimen can extend. The separable members are secured to the grip and to each other. The grip and the adapter do allow preload forces to be applied to the test specimen. However, when the test specimen is located in a temperature chamber, the preloading device is also located in the temperature chamber.

SUMMARY OF THE INVENTION

A test specimen holder for holding a test specimen in a material testing machine that applies force loads to the test specimen includes a base member having a first end coupleable to the material testing machine and a second end remote from the first end. A longitudinal axis extends from the first end to the second end. A body member extends from the second end to the first end and includes an aperture disposed on the longitudinal axis for receiving the test specimen. A displacement device displaces the body member relative to the base member substantially parallel to the longitudinal axis.

In one embodiment, the base member comprises separable base portions that when placed adjacent to each other form the aperture. Each of the body portions engage the base member at the first end so as to limit radial displacement of the body portions away from each other and the longitudinal axis.

BRIEF DESCRIPTION OF THE DRAWINGS

FIG. 5 is an enlarged sectional view of a portion of FIG. 4.

FIG. 6 is a top plan view of a second embodiment of a test specimen holder.

FIG. 7 is a sectional view taken along lines 7—7 of FIG. 6.

FIG. 11 is a sectional view of a fifth embodiment of a test specimen holder of the present invention.

FIG. 15 is a top plan view of an eighth embodiment of the test specimen holder of the present invention.

FIG. 16 is a side elevational view of the test specimen holder of FIG. 15 with portions removed.

DETAILED DESCRIPTION OF THE PREFERRED EMBODIMENTS

Figure 1:
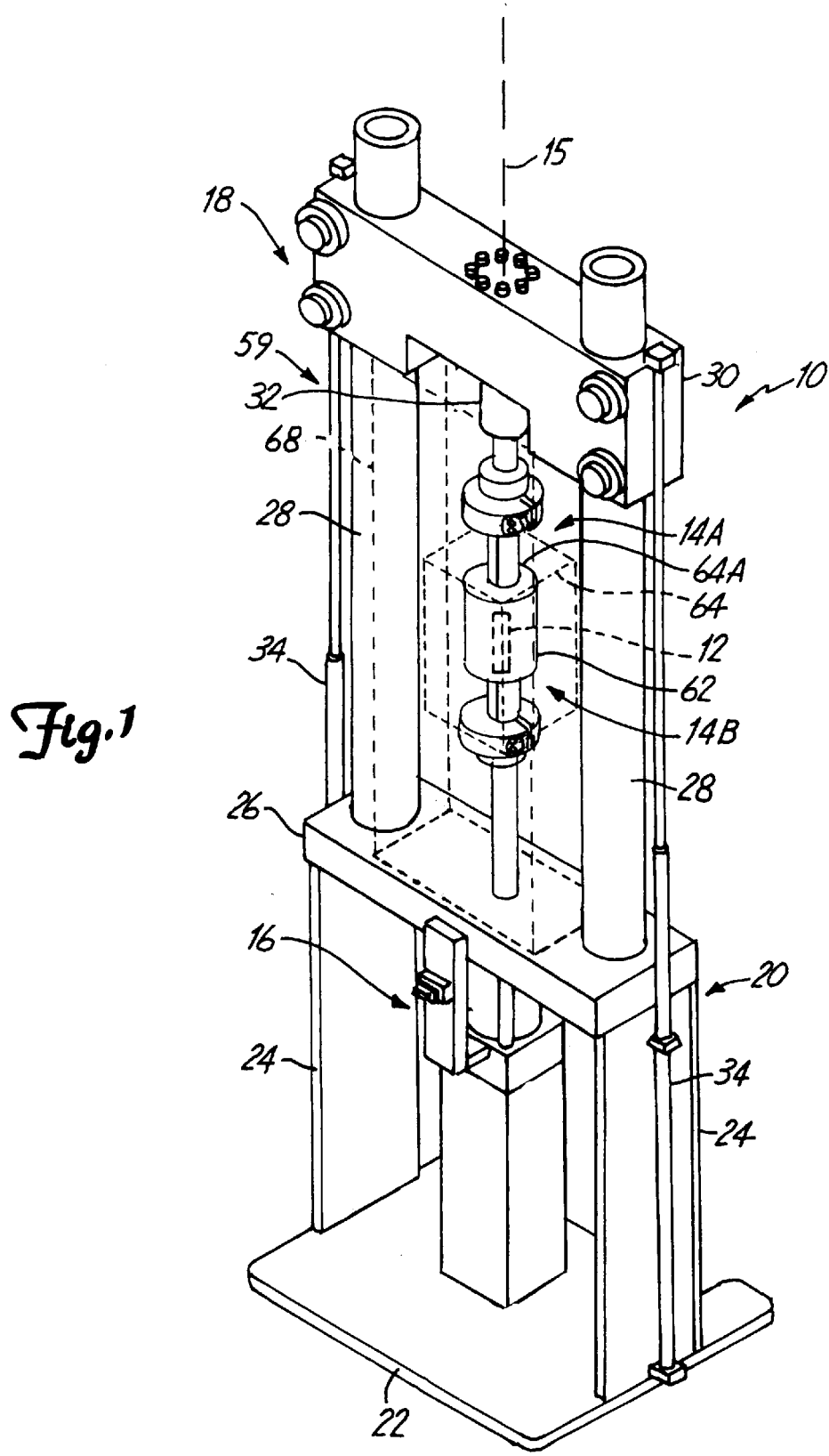
FIG. 1 is a perspective view of a material testing system having test specimen holders of the present invention.
Figure 2:
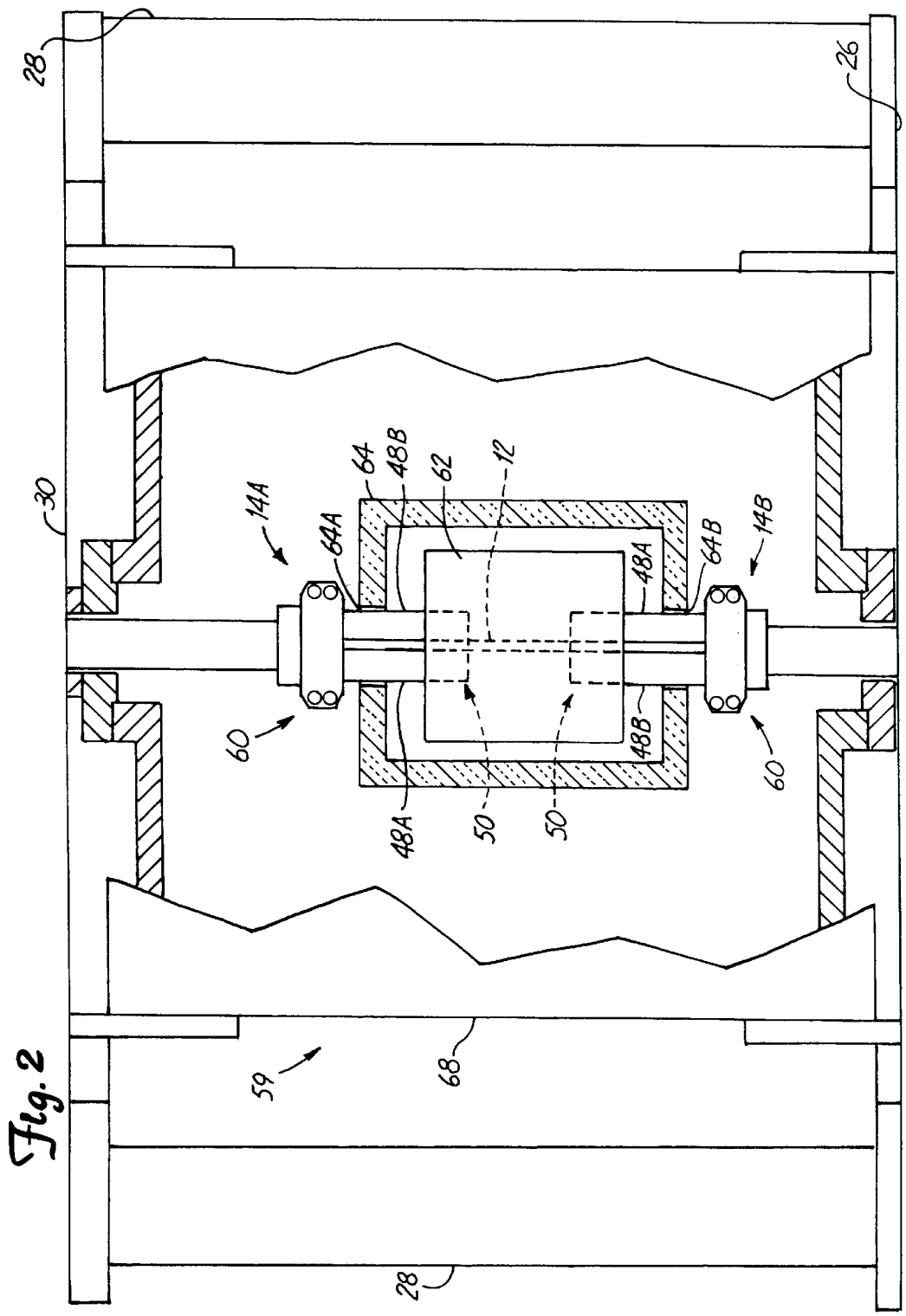
FIG. 2 is an enlarged side elevational view of the material testing system with portions removed.

A material testing system 10 for applying force loads to a test specimen 12 is illustrated in FIGS. 1 and 2. The system 10 includes an upper test specimen holder 14A and a lower test specimen holder 14B of the present invention that hold the test specimen 12 along a longitudinal axis 15. The lower test specimen holder 14B is connected to an actuator 16 through which force loads are applied to the test specimen 12 and reacted against a reaction structure generally indicated at 18.

In the embodiment illustrated, the material testing system 10 includes a frame 20 having a base 22. A pair of support members 24 extend upwardly from the base 22 and are joined together by a crossbeam 26 which provides a stable support surface. A pair of support columns 28 extend upwardly from the crossbeam 26 to a movable crosshead 30. A load cell 32 joins the upper test specimen holder 14A to the crosshead 30. As is known in the art, the load cell 32 provides a signal indicative of tension or compression forces applied to the test specimen 12. The crosshead 30 and the support columns 28 provide the reaction structure 18. Hydraulic lifts 34 move the crosshead 30 to selectively fixed positions.

Figure 3:
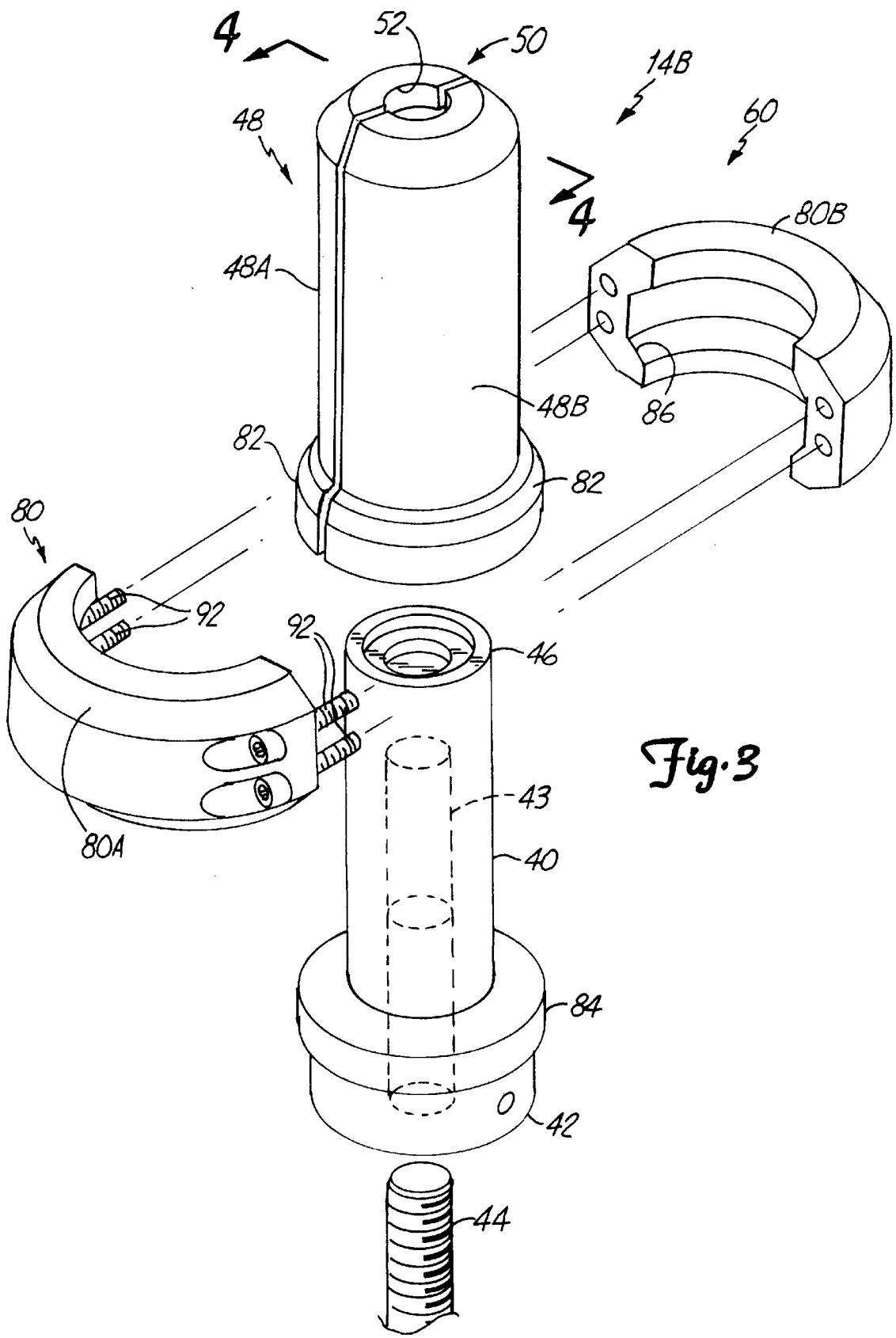
FIG. 3 is an exploded perspective view of a first embodiment of the test specimen holder.

In the embodiment illustrated, the upper test specimen holder 14A is identical to the lower test specimen holder 14B. Referring to FIG. 3 and the lower test specimen holder 14B by way of example, the lower test specimen holder 14B includes a base member 40 having a first end 42 coupleable to a connecting rod 44 of the actuator 16. Preferably, an inner bore 43 extends into the base member 40 to reduce mass.

Figure 4:
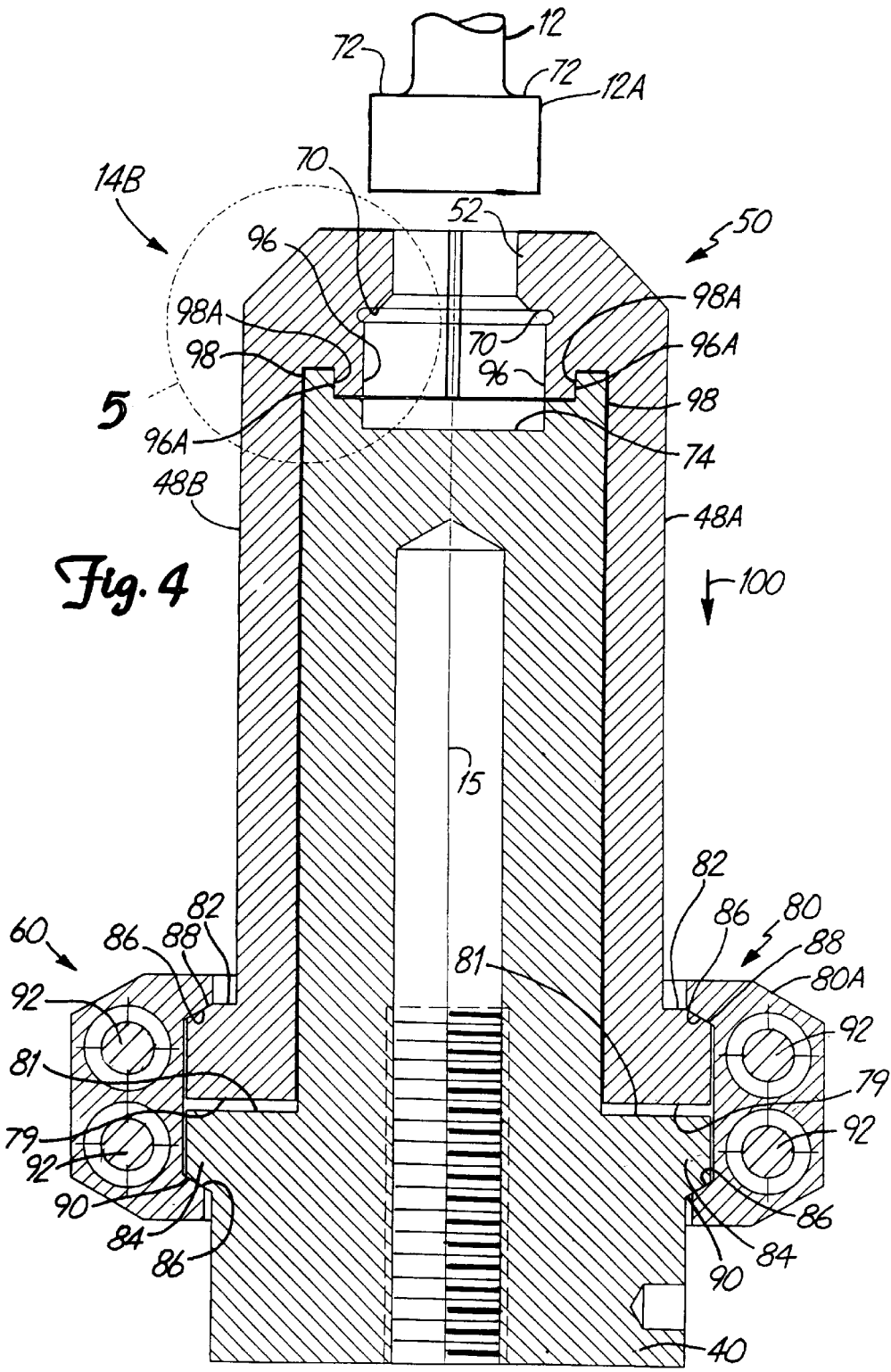
FIG. 4 is a sectional view of the test specimen holder taken along lines 4—4 in FIG. 3.

The base member 40 further includes a second end 46 remote from the first end 42. A body member 48 extends over at least a portion of the base member 40 from the second end 46 to the first end 42. The body member 48 includes an end portion 50 that cooperates with the second end 46 to hold or grip the test specimen 12. Referring also to FIG. 4, the end portion 50 includes an aperture 52 through which the test specimen 12 extends without contact of the surfaces of the aperture 52. A displacement device 60 displaces the body member 48 relative to the base member 40 substantially parallel to the longitudinal axis 15 wherein end surface 79 are displaced toward, but preferably spaced-apart from, a base member 81. The displacement device 60 secures the body member 48 to the base member 40 in order to secure the test specimen 12, and, preferably preload the test specimen 12. Since the upper test specimen holder 14A is substantially identical to the lower test specimen holder 14B, similar components have been identified with the same reference numerals.

The test specimen holders 14A and 14B are particularly useful for holding a test specimen 12 having enlarged end portions, for example, as illustrated in FIG. 4 at 12A. Commonly, the test specimens are cylindrical and can be made, for example, from plastics, ceramics or glass. The test specimen holders 14A and 14B apply compression forces to the end portions of the test specimen 12 that are substantially parallel to the longitudinal axis 15, while applying no or minimal compressive forces that are radial to the longitudinal axis 15. By preloading the end portions 12A, the end portions 12A are held rigid or stationary with respect to each holder 14A, 14B. This allows testing of the test specimen 12 in both tension and compression where test forces pass through zero. The test specimen holders 14A and 14B are elongated in order that, if desired, the test specimen 12 can be tested in an environmental chamber 59 illustrated in FIGS. 1 and 2. The environmental chamber 59 includes a heating or cooling structure 62 that surrounds the test specimen 12. If heating elements are used, a radiation shield 64 surrounds the structure 62 and includes apertures 64A and 64B through which the test specimen holders 14A and 14B extend. If desired, an enclosure 68 can also be used to minimize heat transfer to or from the surrounding environment. By locating the displacement devices 60 remote from the end portions 50, the mass of the test specimen holders 14A and 14B within the environmental chamber 59 is reduced, thereby requiring less heating or cooling by the structure 62. In addition, operation of the displacement device is also located outside of the structure 62. The environmental chamber 59 and accompanying structure 62, radiation shield 64 and enclosure 68 are not a part of the present invention, but demonstrate advantageous features thereof.

In a first embodiment illustrated in FIGS. 1–5, the body member 48 comprises a split-assembly formed from a first portion 48A and a second portion 48B, which when placed adjacent each other form the aperture 52 through which the test specimen 12 extends. Referring to FIG. 4, each body member portion 48A and 48B includes an inner surface 70 that extends about a portion of the longitudinal axis 15 and is engageable with an upper surface 72 of the end portion 12A of the test specimen 12. Preferably, the base member 40 includes a recess 74 for receiving the end portion 12A so as to align the test specimen 12 in the lower test specimen holder 14B and ensure that the test specimen 12 is properly aligned with the aperture 52.

As stated above, the displacement device 60 displaces the body member 48 relative to the base member 40 substantially parallel to the longitudinal axis 15. In the embodiment illustrated, the displacement device 60 comprises a split collar assembly 80. The split collar assembly 80 engages extending flanges 82 on base member portions 48A and 48B, respectively, and an extending flange 84 on the base member 40. The split collar assembly 80 includes a first collar 80A and a second collar 80B. Each collar 80A and 80B includes converging sidewalls 86. The sidewalls 86 engage similarly inclined surfaces 88 on the extending flanges 82. The sidewalls 86 also engage an inclined surface 90 formed on the extending flange 84 on the base member 40. Suitable fasteners 92 join the first collar 80A to the second collar 80B. The converging sidewalls 86 of the split collar assembly 80 initiate displacement of the body member 48 relative to the base member 40.

Referring to FIGS. 4 and 5, flanges 96 on the first and second body portions 48A and 48B engage an annular flange 98 provided on the base member 40. In particular, contact is made between surfaces 96A and 98A which are parallel to the longitudinal axis 15. It is important to note that contact is not made between an end surface 98B of the flange 98 and either of the body portions 48A and 48B. Likewise, contact is not made between end surfaces 96B of the flanges 96 with the base member 40. In this manner, when the displacement device 60 initiates displacement of the body portions 48A and 48B in a direction indicated by arrow 100 (FIG. 4) relative to the base member 40, holding forces are transmitted from the displacement device 60 to the inner surfaces 70 to hold the end portion 12A against the base member 40 without substantial compressive forces radial to the longitudinal axis 15. Contact between the flanges 96 and 98 limits radial displacement of the body portions 48A and 48B away from the longitudinal axis 15 wherein the body portions 48A and 48B slide relative to the base member 40 on the surfaces 96A and 98A.

In an alternative embodiment illustrated in FIGS. 6 and 7, radial displacement of the body portions 48A and 48B away from the longitudinal axis 15 is limited by tabs 104 and 106. Tabs 104 are provided on the first body portion 48A and the second body portion 48B. The tabs 104 engage the tabs 106 provided on the base member 40. In this embodiment, planar surfaces 104A and 106A engage each other rather than the semi-cylindrical surfaces 96A and the annular surface 98A described in the previous embodiment.

Figure 8:
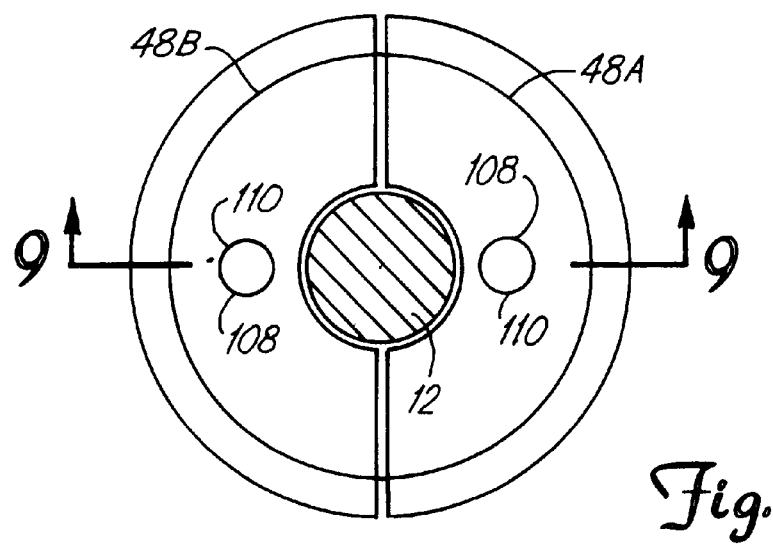
FIG. 8 is a third embodiment of a test specimen holder of the present invention.
Figure 9:
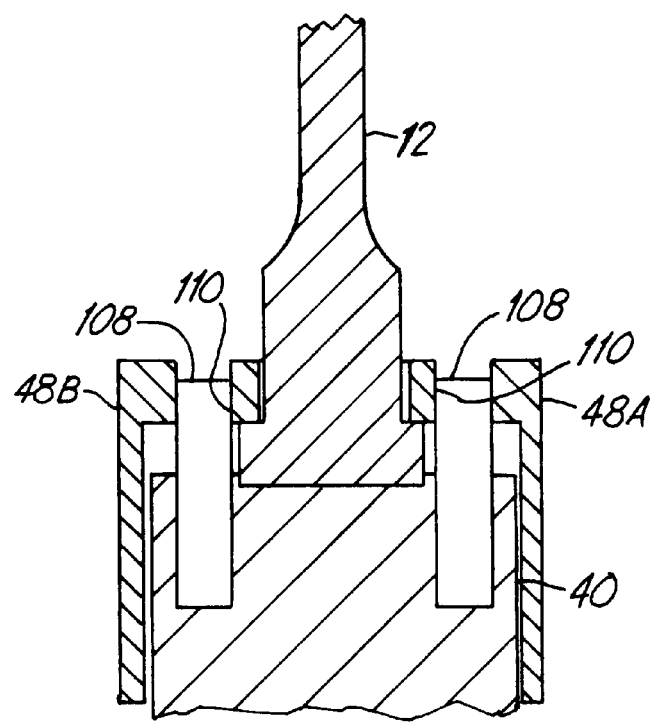
FIG. 9 is a sectional view of the test specimen holder taken along lines 9—9 in FIG. 8.

In yet another embodiment illustrated in FIGS. 8 and 9, pins 108 extend through apertures 110 provided in the first body portion 48A and the second body portion 48B. Interaction of the pins 108 with walls forming the apertures 110 limits radial displacement of the first body portion 48A and the second body portion 48B from the longitudinal axis 15. As appreciated by those skilled in the art, pins can be provided on the first body portion 48A and the second body portion 48B, rather than on the base member 40, to project into suitable apertures or recesses provided in the base member 40.

Figure 10:
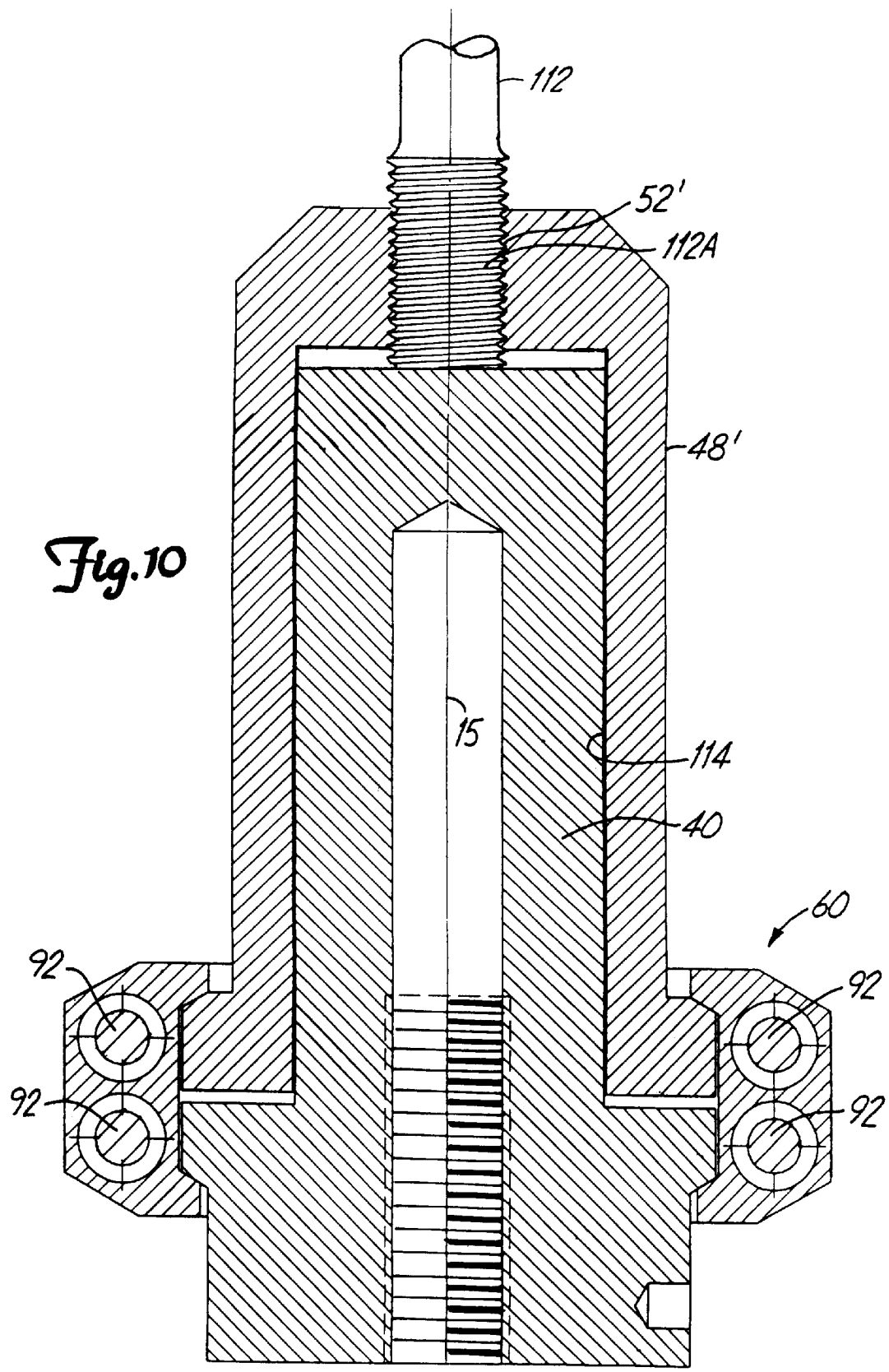
FIG. 10 is a sectional view of a fourth embodiment of a test specimen holder of the present invention.

In another embodiment illustrated in FIG. 10, a body member 48' is a single structure unlike the previous embodiment where the body member 48 comprises body portions 48A and 48B. In this embodiment, the body member 48' includes a threaded aperture 52' that receives a threaded portion 112A of a test specimen 112. The body member 48' includes a bore 114 that receives the base member 40. The displacement device 60 operates as described above to displace the body member 48' relative to the base member 40 along the longitudinal axis 15 in order to apply preload forces to end portions 12A.

FIGS. 11–16 illustrate alternative embodiments of the displacement device 60. In FIG. 11, the displacement device 60 comprises a threaded collar 120. The collar 120 is a single unitary element having a bore 122 with a first opening 122A and a second opening 122B that is smaller than the first opening 122A. The smaller opening 122B is large enough to allow the body member 48 to extend therethrough, but is small enough such that a flange 124 is formed to engage the flange 82 of the body member 48. Threads 126 are provided in the bore 122 and engage corresponding threads 128 provided on the base member 40. When the collar 120 is rotated relative to the base member 40, the body member 48 is displaced linearly relative to the base member 40. The collar 120 can be used with the split body member 48 illustrated in FIGS. 1–5 or with the integral body member 48' illustrated in FIG. 10.

Figure 12:
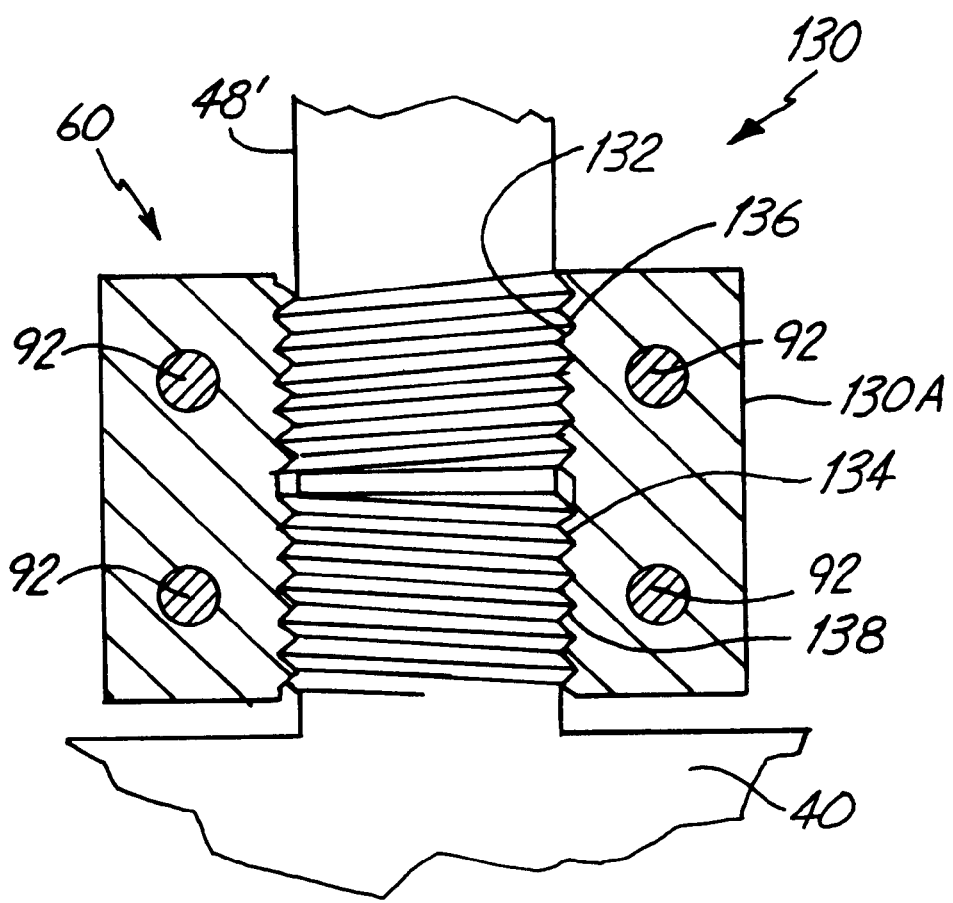
FIG. 12 is a sectional view of a sixth embodiment of a test specimen holder of the present invention.

In FIG. 12, the displacement device 60 comprises a split collar assembly 130. Generally, the split collar assembly 130 includes identical collar portions, one of which is illustrated at 130A. The split collar assembly 130 is similar to the split collar assembly 80 illustrated in FIGS. 1–5 and are held together with the fasteners 92. Each split collar portion includes a portion of threads 132 formed in a first direction, and a second portion of threads 134 formed in a second direction. When the split collar assembly 130 is joined together with the fasteners 92, the first portions of threads 132 form threads in the first direction, for example, right-hand threads, while the second portions of threads 134 form threads in the second direction, for example, left-hand threads. In this embodiment, the body member 48' includes threads 136 adapted to engage the first threaded portions 132 while the base member 40 includes threads 138 adapted to engage the second threaded portions 134. After the body member 48' has been positioned over the base member 40 and the split collar assembly 130 has been formed, rotation of the split collar assembly 130 causes the body member 48' to be displaced relative to the base member 40. The split collar assembly 130 can be used with either the integral body member 48' illustrated in FIG. 10 or with the split body member 48 illustrated in FIGS. 1–5, if portions of the threads 136 are provided on each of the body member portions 48A and 48B.

Figure 13:
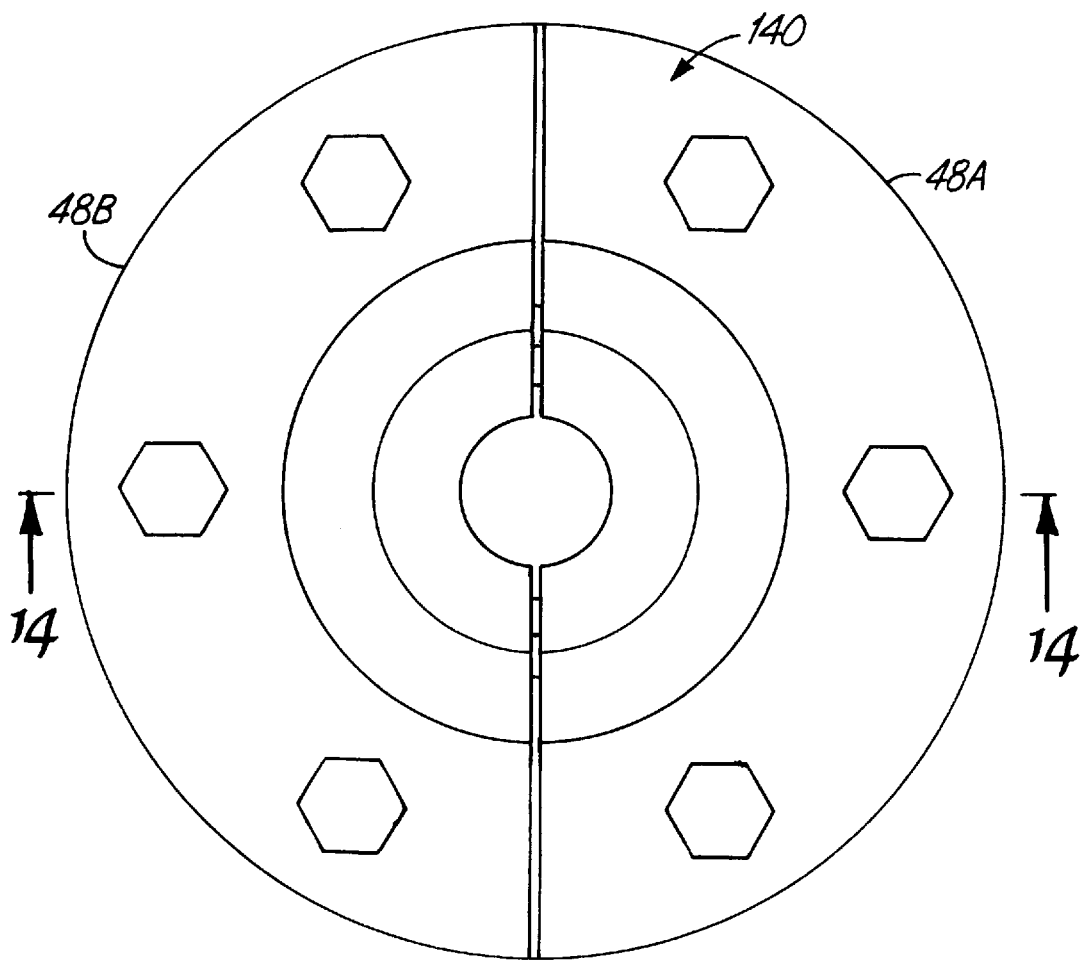
FIG. 13 is a top plan view of a seventh embodiment of a test specimen holder of the present invention.
Figure 14:
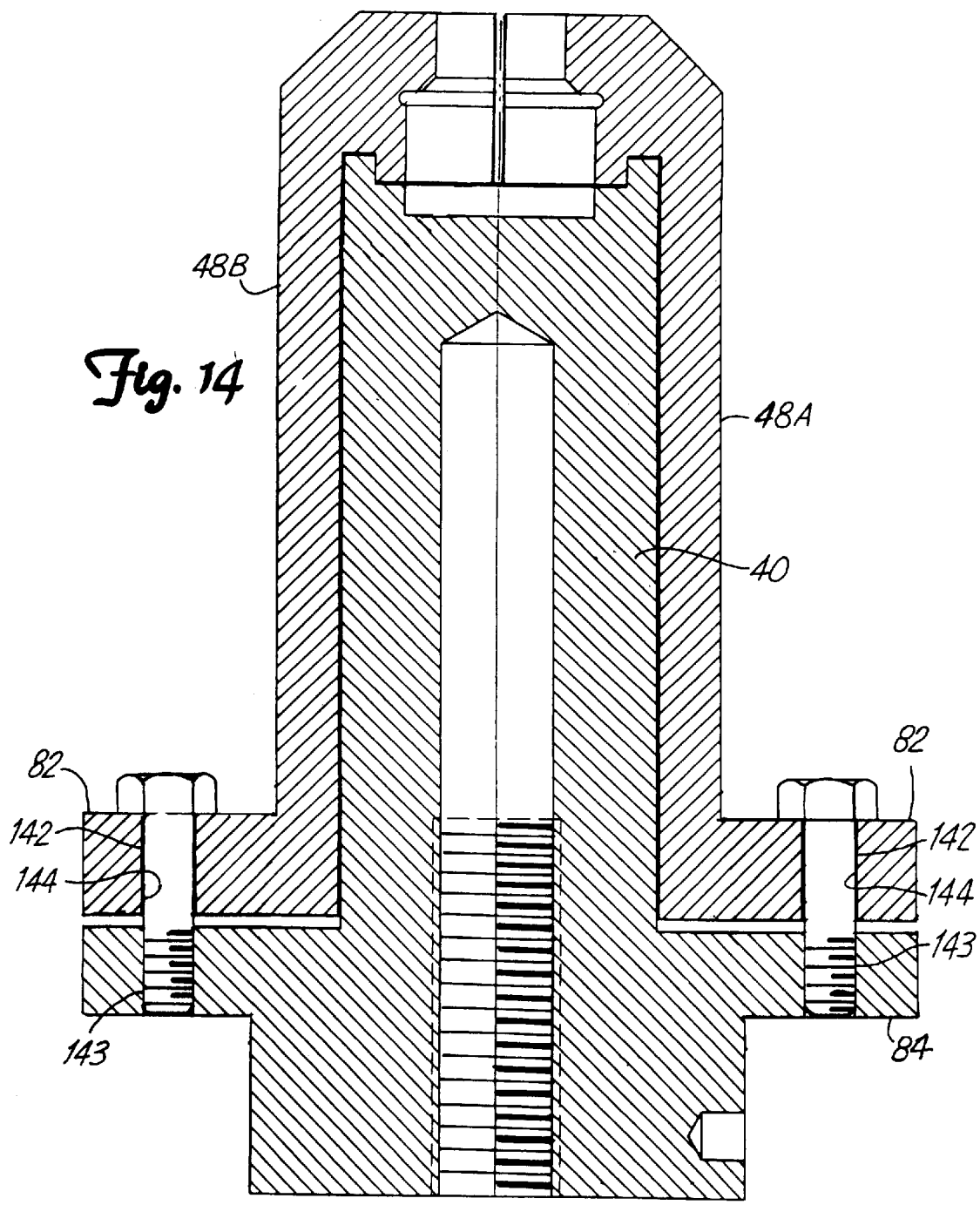
FIG. 14. is a sectional view of the test specimen holder taken along lines 14—14 in FIG. 13.

In FIGS. 13–14, the displacement device 60 comprises a plurality of fasteners 140. Each fastener of the plurality of fasteners 140 includes a rod portion 142 extending through corresponding apertures 144 provided in the flanges 82. In this embodiment, threaded apertures 143 are provided in the flange 84 of the base member 40 to receive threaded portions of the rods 142. As appreciated by those skilled in the art, threaded apertures can be provided in the body member 48 rather than in the base member 40, wherein the fasteners 140 extend through smooth apertures provided in the base member 40. This embodiment can be used with either the split body member 48 illustrated in FIGS. 1–5 or with the integral base member 48' illustrated in FIG. 10.

In FIGS. 15–16, the displacement device 60 comprises a cam assembly 150. The cam assembly 150 includes rotatable cams 152A and 152B. In this embodiment, the cams 152A and 152B rotate about axes 154A and 154B, respectively. Suitable fasteners 156 retain the cams 152A and 152B on the base member 40. Each cam 152A and 152B, includes a first portion 160 and a second portion 162 that is thicker than the first portion 160. As the cams 152A and 152B are rotated about each respective axis 154A and 154B, the cams 152A and 152B engage the flange 82 of the body member 48. The cams 152A and 152B rotate in a fixed plane so that the second portions 162 initiate displacement of the body member 48 relative to the base member 40. Recesses 161 can be provided in the cams 152A and 152B to allow easy removal of the body member 48. Levers 164A and 164B are attached to the cams 152A and 152B, respectively, in order to aid in rotation. This embodiment can be used with either the split base member 48 illustrated in FIGS. 1–5, or with the integral base member 48' illustrated in FIG. 10.

Although the present invention has been described with reference to preferred embodiments, workers skilled in the art will recognize that changes may be made in form and detail without departing from the spirit and scope of the invention.

What is claimed is:

1. A test specimen holder for holding a test specimen in a material testing machine applying force loads, the test specimen holder comprising:
   an elongated base member having a first end adapted to fixedly couple to the material testing machine, a second end remote from the first end, and a longitudinal axis extending from the first end to the second end;
   an elongated body member positioned over the base member and the base and body member coextending along a longitudinal extent aligned with the longitudinal axis the body member being operably coupled to the base member for slidable movement relative to the base member along the longitudinal axis to provide an axial retaining force along the longitudinal axis for retaining the test specimen against displacement without imparting significant radial compressive force to the test specimen, the body member including a locking surface adapted to engage the test specimen, the base member including a locking surface, the locking surfaces of the body member and base member cooperating to axially retain the test specimen for operation, said base and body member being removably coupled at a location longitudinally spaced from the locking surfaces to form a locking cavity for a test specimen between locking surfaces; and
   an adjustable connecting means operably coupled to the base and body member for removably coupling the body member to the base member for selectively loading and unloading a test specimen into the locking cavity, the adjustable connecting means being adjustable between opposed limit positions to secure a specimen in the locking cavity and provide an axial preload force to the specimen retain thereby, without imparting a significant radial compressive force.

2. The test specimen holder of claim 1 wherein the means for removably coupling secures the body and base flanges in spaced relation.

3. The test specimen holder of claim 2 wherein the means for removably coupling comprises a clamp.

4. The test specimen holder of claim 3 wherein the clamp includes a cam at least partially rotatable about a cam axis, the cam including a sloped camming surface for adjustably securing the body member relative to the base member via rotation of the cam about the cam axis to adjust the locking surfaces of the base and body members to provide a desired preload force to a test specimen.

5. The test specimen holder of claim 3 wherein the clamp includes a first clamp member for engaging the base flange and the body flange, a second clamp member for engaging the base flange and the body flange remote from the first clamp member, and means for securing the first clamp member relative to the second clamp member.

6. The test specimen holder of claim 5 wherein each clamp member includes converging clamp surfaces.

7. A test specimen holder for holding a test specimen in a material testing machine applying force loads, the test specimen holder comprising:

an elongated base member having a first end adapted to fixably couple to the material testing machine, a second end remote from the first end, and a longitudinal axis extending from the first end to the second end;

an elongated body member positioned over the base member and the base and body member coextending along a longitudinal extent aligned with the longitudinal axis the body member being operably coupled to the base member for slidable movement relative to the base member along the longitudinal axis to provide an axial retaining force along the longitudinal axis for retaining the test specimen against displacement without imparting significant radial compressive force to the test specimen, the body member including a locking surface adapted to engage the test specimen, the base member including a locking surface, the locking surfaces of the body member and base member cooperating to axially retain the test specimen for operation said base and body members being removable coupled at a location spaced from the locking surfaces to form a locking cavity for a test specimen between locking surfaces; and means for removably coupling the body member to the base member operably coupled to the base and body member for selectively loading and unloading a test specimen into the locking cavity, and supplying an axial preload force without imparting a significant radial compressive force, the body member comprising a first body member portion and a second body member portion, each portion including locking surfaces, the first body member portion and second body member portion being secured at a position spaced from the locking surfaces so that the locking surfaces are biased radially outwardly, the first body member portion and second body member portion being secured by the means for coupling the body member to the base member, the first and second body member portions including stop means for limiting radial displacement of locking surfaces of the first body member portion from the second body member portion.

8. The test specimen holder of claim 7 wherein the stop means for limiting radial displacement comprises cooperating engaging flanges formed on the first body member portion, the second body member portion and the base member.

9. The test specimen holder of claim 8 wherein the flanges engage only on surfaces parallel to the longitudinal axis.

10. The test specimen holder of claim 7 wherein the stop means for limiting radial displacement comprises a first pin extending between the first body member portion and the base member, and a second pin extending between the second body member portion and the base member.

11. A test specimen holder for holding a test specimen in a material testing machine applying force loads, the test specimen holder comprising:

an elongated base member having a first end adapted to fixably couple to the material testing machine, a second end remote from the first end, and a longitudinal axis extending from the first end to the second end;

an elongated body member including a locking surface adapted to engage a test specimen, the base member including a locking surface, the locking surfaces of the body member and base member cooperating to axially retain the test specimen for operation, the base member and body member being formed of inner and outer cylindrical members coaxially aligned along an elongated extent, the outer member having an end cap, the end cap of the outer member and an end surface of the inner member forming opposed radially aligned end surfaces, the locking surfaces being recessed from the end surface of the inner member and end surface of the end cap of the outer member and formed by recessed cavities formed in the inner member and end cap of the outer member, said base and body member being removably coupled at a location spaced from the locking surfaces to form a locking cavity for a test specimen between locking surfaces;

an adjustable connecting means operably coupled to the base and body member for removably coupling the body member to the base member for selectively loading and unloading a test specimen into the locking cavity, and being longitudinally adjustable between opposed limit positions to secure a specimen in the locking cavity and supply an axial preload force to the test specimen without imparting a significant radial compressive force.

\* \* \* \* \*